United States Patent
Albiez et al.

(10) Patent No.: US 6,815,551 B2
(45) Date of Patent: Nov. 9, 2004

(54) PROCESSES FOR CONCENTRATING TOCOPHEROLS AND/OR STEROLS

(75) Inventors: Wolfgang Albiez, Neuss (DE); William G. Kozak, Hatfield, PA (US); Thorsten Louwen, Essen (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 89 days.

(21) Appl. No.: 10/343,776

(22) PCT Filed: Aug. 1, 2001

(86) PCT No.: PCT/EP01/08877

§ 371 (c)(1),
(2), (4) Date: Feb. 4, 2003

(87) PCT Pub. No.: WO02/12222

PCT Pub. Date: Feb. 14, 2002

(65) Prior Publication Data

US 2003/0158429 A1 Aug. 21, 2003

(30) Foreign Application Priority Data

Aug. 7, 2000 (DE) ......................................... 100 38 457

(51) Int. Cl.$^7$ ........................................... C07D 311/72
(52) U.S. Cl. ...................................................... 549/413
(58) Field of Search ........................................... 549/413

(56) References Cited

U.S. PATENT DOCUMENTS

| 3,335,154 A | 8/1967 | Smith |
| 3,840,570 A | 10/1974 | Julian |
| 4,454,329 A | 6/1984 | Takagi et al. |
| 5,487,817 A | 1/1996 | Fizet |

FOREIGN PATENT DOCUMENTS

| DE | 31 26 110 A1 | 4/1982 |
| DE | 196 52 522 C2 | 6/1998 |
| DE | 199 16 034 C1 | 8/2000 |
| EP | 0 610 742 B1 | 8/1994 |
| EP | 0 656 894 B2 | 6/1995 |
| WO | WO 94/05650 A | 3/1994 |
| WO | WO 97/21697 A1 | 6/1997 |

OTHER PUBLICATIONS

Ullmann's Encyclopedia of Industrial Chemistry, vol. A27, (1996), pp. 478–488, XP002183270, Weinheim.
G. Dieckelmann et al., The Basics of Industrial Oleochemistry, Peter Pomp GmbH (Ed.), (1988), pp. 36–41.

Primary Examiner—Taofiq Solola
(74) Attorney, Agent, or Firm—Aaron R. Ettelman

(57) ABSTRACT

A process for concentrating sterols and/or tocopherols from mixtures of fats and fatty derivatives and from residues left after they have been worked up is described. After splitting of the glycerides by hydrolysis and subsequent removal of the free fatty acids by distillation, the tocopherol/sterol esters still present are largely split into free tocopherols/sterols by an additional hydrolysis step.

5 Claims, No Drawings

PROCESSES FOR CONCENTRATING TOCOPHEROLS AND/OR STEROLS

BACKGROUND OF THE INVENTION

The production of sterols and tocopherols from a variety of animal and vegetable raw materials, more particularly vegetable oils, such as wheat germ oil, corn oil, soybean oil, safflower oil, peanut oil, cottonseed oil, sunflower oil, rapeseed oil, palm oil and other oils, has already been variously described in the literature, cf. WO 9721697 and EP 0 656 894 where the prior art is extensively acknowledged. Natural vegetable oils contain only small quantities of tocopherol. Accordingly, the described processes always involve a concentration step. The term "tocopherol" is intended to encompass the tocopherol derivatives of tocotrienol and tocol.

Accordingly, the most important natural sources of tocopherol are not the vegetable oils themselves, but rather the steam distillates—also known as deodorizer distillates— obtained in the deodorization of animal and vegetable oils. Although the tocopherols are obtained in concentrated form in this case, they are mixed with sterol and sterol esters, free fatty acids and triglycerides. According to EP 0 656 894, the free fatty acids present in a mixture containing tocopherol, fats and/or fatty derivatives, more particularly fatty acids, and optionally sterol and/or sterol derivatives are esterified with a lower alcohol. The mixture is then transesterified with a lower alcohol in the presence of a basic catalyst. After the transesterification, the excess lower alcohol is distilled of from the reaction mixture. The transesterification catalyst and the glycerol present, if any, are removed and the fatty acid alkyl ester is distilled off from the mixture. However, the sterol yield is unsatisfactory. It is improved in a process described in DE 199 16 034. These processes may be used for many different starting mixtures and do not involve the use of toxicologically and ecologically unsafe solvents. Nevertheless, the transesterification catalysts used therein frequently contain metals and may also be classified as an environmental hazard.

Accordingly, the problem addressed by the present invention was to provide a process for the simultaneous production of tocopherol and sterol which would be applicable to many different starting mixtures, would not involve the use of toxicologically and ecologically unsafe solvents, would use even low-concentration starting materials sparingly and would still give high yields without the use of metal-containing catalysts. In addition, the process would be economically workable on an industrial scale.

BRIEF SUMMARY OF THE INVENTION

The present invention relates, in general, to the production of sterols and tocopherols and more particularly to a process for isolating sterols and tocopherols from mixtures of fats and fatty derivatives and from residues left after they have been worked up.

The present invention relates to a process for concentrating and isolating sterols and/or tocopherols from sterol- and/or tocopherol-containing mixtures of fats and/or fatty derivatives containing glycerides, characterized in that (a) a mixture is hydrolyzed to split the glycerides present into free fatty acids and glycerol, (b) the glycerol-containing hydrolysis water is removed, (c) the free fatty acids and readily volatile unsaponifiable components are removed by distillation, (d) one or more additional hydrolyses of the distillation residue is/are carried out to split the sterol esters into free fatty acids and free sterols, (e) the hydrolysis water is removed and (f) the fatty acids formed are removed by distillation.

It has been found that, after splitting of the glycerides by hydrolysis and subsequent removal of the free fatty acids by distillation, the sterol esters still present can largely be split into free sterols by another hydrolysis step. This characterizes the process according to the invention for concentrating and isolating sterols and optionally tocopherols from sterol- and/or tocopherol-containing mixtures of fats and/or fatty derivatives which contain hydrolyzable products, such as sterol esters and/or glycerides. The advantage of the process according to the invention is that it does not involve the use of metal-containing catalysts (such as, for example, zinc, tin, sodium) or toxicologically and ecologically unsafe solvents, and that even starting materials of low concentration, for example physically refined deodorizer distillates, can be economically used. The required degree of concentration can be controlled through the number of hydrolysis steps.

Deodorizer distillates of the oils such as, for example, rapeseed oil, sunflower oil, palm oil, palm kernel oil, coconut oil, soybean oil, corn oil and cottonseed oil, may be used as the starting material. Mixtures of different oils and deodorizer distillates may be used although the deodorizer distillates of individual oils, more particularly rapeseed oil, sunflower oil or soybean oil deodorizer distillates, are preferred.

DETAILED DESCRIPTION OF THE INVENTION

First Hydrolysis Step (a)

According to the invention, preferably only the tri-, di- and monoglycerides are reacted with water (hydrolysis) under relatively mild conditions in the first step of the process to form free fatty acids and glycerol. According to the invention, the sterol esters remain substantially bound. Only a small amount of free sterols is formed. Water is preferably used in a quantity of 30 to 100% by weight and more particularly 40 to 60% by weight, based on the material to be worked up. The splitting reaction preferably takes place at temperatures of 190° C. to 250° C. and more particularly at temperatures of 210 to 220° C., under the associated steam pressure and in the absence of a catalyst. However, higher temperatures, more particularly above 220° C., lead to unwanted polymerization, particularly in the case of unsaturated fatty acids and glycerides. The higher the temperature, the shorter the reaction time. Reactions times of 1 to 6 hours and more particularly 2 to 4 hours are normal for the selected temperature range. Both conventional stirred batch reactors and continuous reactors, for example turbulent-flow reactors, may be used as the reactor (see G. Dieckelmann, I. J. Heinz, The Basics of Industrial Oleochemistry (1988)).

Removal of the Hydrolysis Water (b)

The glycerol-containing hydrolysis water is removed discontinuously or continuously via phase separation, depending on the procedure adopted.

Removal of the Free Fatty Acids (c)

The so-called split fatty acids formed during the hydrolysis and the free fatty acids already present in the starting product are distilled off overhead in the next step. Low-boiling unsaponifiable components are partly removed at the same time. In the case of tocopherol-containing starting materials, a distillation column equipped with a high-performance packing (for example Sulzer Optiflow) is preferably used. A wiped thin-layer evaporator through which the product passes just once is preferably used as the bottom evaporator. In this way, the tocopherols and sterols are left in the residue and at the same time are subjected to very little heat stress. The fractional distillation is typically carried out at a head pressure of 0.5 to 10 mbar, preferably 1 to 6 mbar, a bottom pressure of 1 to 30 mbar, more particularly 5 to 10 mbar and at bottom temperatures of 200 to 350° C., more particularly 250 to 300° C.

The residue thus deacidified and distinctly reduced in relation to the starting quantity essentially contains only the tocopherols, the free sterols and the bound sterol esters and residues of free fatty acids and partial glycerides.

Additional Hydrolysis Steps (d)

According to the invention, the first distillation residue is subsequently re-hydrolyzed under pressure with water under comparatively mild conditions in the absence of a catalyst, the sterol esters present mainly being split into free sterols and free fatty acids. Water is preferably used in a quantity of 30 to 200% by weight and more particularly 60 to 100% by weight, based on the material to be worked up. The splitting reaction preferably takes place at temperatures of 190° C. to 250° C. and more particularly 210° C. to 220° C. under the associated steam pressure. The reaction times are preferably in the range from 3 to 12 hours and more particularly 5 to 7 hours. Stirred batch autoclaves are preferably used as the reactor to guarantee the relatively long reaction time required to hydrolyze the sterol esters. According to the invention, another hydrolysis step may optionally be carried out with steam, depending on the starting material.

Removal of the Hydrolysis Water II (e)

After the reaction, the hydrolysis water is removed via a phase separation.

Removal of the Fatty Acids II (f)

The hydrolysis product thus obtained now essentially consists solely of the "split" fatty acids newly formed, the tocopherols and the free sterols. In the following process step, the fatty acids are distilled off overhead in a preferably similar apparatus configuration and preferably under similar operating conditions to the first fatty acid distillation.

EXAMPLE

A soybean oil distillate of the following composition was used as the starting material (deodorizer distillate):

|  | % by weight |
| --- | --- |
| Fatty acids | 31.5 |
| Tocopherols | 12.2 |
| Sterols | 8.2 |
| Sterol esters | 19.5 |
| Glycerides | 17.0 |
| Other unsaponifiables | 11.2 |

1000 g of the above deodorizer distillate and 500 g of deionized water were introduced into an autoclave and heated with stirring to 220° C. After a reaction time of 3 hours, the autoclave was cooled and the hydrolysis product was separated from the glycerol-containing hydrolysis water via a phase separator. After drying of the product, a mixture of 970 g with the following composition is obtained:

|  | % by weight |
| --- | --- |
| Fatty acids | 49.6 |
| Tocopherols | 12.6 |
| Sterols | 12.0 |
| Sterol esters | 14.3 |
| Other unsaponifiables | 11.5 |

The fatty acids were distilled off overhead in a distillation column equipped with a fabric packing and a thin-layer evaporator as the bottom evaporator. The head pressure of the column was 1.8 mbar and the temperature of the heating medium 280° C. The distillate was free from tocopherols and sterols and the bottom product was reduced to 450 g from 1000 g of the starting quantity.

The bottom product of the distillation was the starting material for the hydrolysis of the sterols and had the following composition:

|  | % by weight |
| --- | --- |
| Fatty acids | 4.4 |
| Tocopherols | 26.9 |
| Sterols | 25.7 |
| Sterol esters | 30.5 |
| Other unsaponifiables | 12.4 |

400 g of the bottom product and 400 g of deionized water were introduced into an autoclave and heated with stirring to 220° C. After a reaction time of 6 hours, the autoclave was cooled and the hydrolysis product was separated from the hydrolysis water in a phase separator.

After drying of the product, the following composition was determined:

|  | % by weight |
| --- | --- |
| Fatty acids | 14.9 |
| Tocopherols | 26.9 |
| Sterols | 42.2 |
| Sterol esters | 3.6 |
| Other unsaponifiables | 12.4 |

The fatty acids were distilled off overhead under the same conditions in the same distillation column. The distillation residue had the following composition:

|  | % by weight |
| --- | --- |
| Fatty acids | 1.5 |
| Tocopherols | 31.2 |
| Sterols | 48.8 |
| Sterol esters | 4.2 |
| Other unsaponifiables | 14.3 |

More than 90% of the free sterol and/or 95% of the tocopherol from the mixtures of the fats and/or fatty derivatives can be concentrated by repeated hydrolysis steps by this process.

What is claimed is:

1. A process for concentrating sterols and/or tocopherols, said process comprising:
   (a) providing a fatty mixture comprising glycerides, readily volatile unsaponifiable components and at least one component selected from the group consisting of tocopherols and sterols;
   (b) hydrolyzing the glycerides present in the mixture to provide free fatty acids and glycerol-containing hydrolysis water;
   (c) removing the glycerol-containing hydrolysis water;
   (d) distilling the free fatty acids and readily volatile unsaponifiable components to provide a distillation residue comprising esters of the at least on component selected from the group consisting of tocopherols and sterols;
   (e) hydrolyzing the distillation residue to split the esters into free fatty acids and the at least one component,
   (f) removing the hydrolysis water; and
   (g) distilling the free fatty acids.

2. The process according to claim 1, wherein the fatty mixture is selected from the group consisting of fatty acid distillation residues and deodorizer distillates.

3. The process according to claim 1, wherein the fatty mixture comprises a deodorizer distillate of an oil selected from the group consisting of rapeseed oil, sunflower oil, palm oil, palm kernel oil, coconut oil, soybean oil, corn coil, cottonseed oil and mixtures thereof.

4. The process according to claim 1, wherein the fatty mixture comprises a deodorizer distillate of soybean oil.

5. The process according to claim 1 wherein the fatty mixture comprises free fatty acids, sterol esters and glycerides.

* * * * *